United States Patent
Hu et al.

(10) Patent No.: US 7,229,768 B2
(45) Date of Patent: Jun. 12, 2007

(54) UNIVERSAL G-PROTEIN COUPLED RECEPTOR REPORTER CONSTRUCTS

(75) Inventors: Yinghe Hu, San Diego, CA (US); Cecilia Jiang, San Diego, CA (US)

(73) Assignee: IRM LLC, Hamilton (BM)

( * ) Notice: Subject to any disclaimer, the term of this patent is extended or adjusted under 35 U.S.C. 154(b) by 139 days.

(21) Appl. No.: 10/759,740

(22) Filed: Jan. 16, 2004

(65) Prior Publication Data

US 2005/0158813 A1    Jul. 21, 2005

(51) Int. Cl.
  *C12Q 1/68*    (2006.01)
(52) U.S. Cl. .................. 435/6; 435/320.1; 435/325
(58) Field of Classification Search ............... 435/6, 435/320.1; 536/23.1
  See application file for complete search history.

(56) References Cited

OTHER PUBLICATIONS

Jiang et al. Generation of a bioactive neuropeptide in a cell-free system Anal. Biocehm 316 (2003) 34-40.*
Friedman, et al. Processing of Prothyrotropin-Releasing Hormone (Pro-TRH) by Bovine Intermediate Lobe Secretory Vesicle Membrane PC1 and PC2 Enzymes. Ednocrinology, 1995. vol. 136, No. 10, pp. 4462-4472.
Nillni, et al. Posttranslational Processing of Progrowth Hormone-Releasing Hormone. Endocrinology, 1999. vol. 140, No. 12, p. 5817-5827.
MacDonald, et al. Posttranslational Processing of Alpha-, Beta-, and Gamma-Preprotachykinins. The Journal of Biological Chemistry, 1988. vol. 263, No. 29, Issue of Oct. 15, p. 15176-15183.
Schaner, et al. Processing of Prothyrotropin-releasing Hormone by the Family of Prohormone Convertases. The Journal of Biological Chemistry, 1997, vol. 272, No. 32, Issue of Aug. 8, p. 19958-19968.
Huynh, Hung. Post-transcriptional and post-translational regulation of insulin-like growth factor binding protein-3 and -4 by insulin-like growth factor-I in uterine myometrial cells. Growth Hormone & IGF Research 2000, vol. 10, p. 20-27.
Hook, et al. Production of Radiolabeled Neuropeptide Precursors by in vitro Transcription and Translation, Pept. Res. 9(4): pp. 183-187, 1996.
Fitzgerald et al., Analyt. Biochem. 275: 54-61, 1999.
White et al. Evaluation of the Effectiveness of DNA-Binding Drugs to Inhibit Transcription Using the c-fos Serum Response Element as a Target. Biochemistry, vol. 39, pp. 12262-12273, 2000.
Sho et al. Novel Roles of Specific Isoforms of Protein Kinase C in Activation of the c-fos Serum Response Element. Molecular and Cellular Biology, Feb. 1999, pp. 1313-1324.
Sealy et al. Regulation of the cfos Serum Response Element by C/EBP/β. Molecular and Cellular Biology, Mar. 1997, pp. 1744-1755.
Jiang et al. Generation of a bioactive neuropeptide in a cell-free system. Analytical Chemistry, 316, 2003, pp. 34-40.

* cited by examiner

*Primary Examiner*—James Ketter
(74) *Attorney, Agent, or Firm*—Timothy L. Smith, Jr.; Genomics Institute of the Norvartis Research Foundation

(57) ABSTRACT

The present invention provides universal G protein-coupled receptor (GPCR) reporter constructs. The constructs comprise a serum response element, a cAMP response element, and a multiple response element. These reporter constructs are able to detect activities of all GPCRs examined. Further provided by the present invention are host cells harboring a universal GPCR reporter construct of the invention, as well as assays for detecting modulators of GPCRs using the host cells.

19 Claims, No Drawings

UNIVERSAL G-PROTEIN COUPLED RECEPTOR REPORTER CONSTRUCTS

FIELD OF THE INVENTION

This invention relates generally to G-protein coupled receptors. In particular, the invention relates to compositions and methods for assaying activities of G-protein coupled receptors, and for identifying modulators of G-protein coupled receptors. The invention finds applications in drug discovery and pharmaceutical industry.

BACKGROUND OF THE INVENTION

G-protein-coupled receptors constitute the largest family of cell surface receptor proteins. There are three major families of GPCRs, Gs-, Gi-, and Gq-coupled receptors. Upon activation, different GPCRs stimulate a number of signal transduction pathways. For example, Gs-coupled receptor increases while Gi-coupled receptor decreases cAMP production. Therefore, these two different GPCRs can activate or inhibit the cAMP-response element. On the other hand, Gq-coupled receptor increases intracellular calcium concentration and activates the multiple-response element.

Many human diseases are associated with the dysfunction of GPCRs. GPCRs are the most attractive therapeutic targets in the pharmaceutical industry. A large number of technologies have been developed to detect GPCRs activity. However, these technologies can only be used with certain types of GPCRs. There are no existing assay systems that can be employed to universally detect ligand-binding activities of all types of GPCRs.

Therefore, a need exists for real universal assay system to identify ligands or modulators of various GPCRs from different biological samples. The present invention fulfills this and other needs.

SUMMARY OF THE INVENTION

The present invention provides compositions and methods for detecting activities of G-protein-coupled receptors (GPCRs). In one aspect, the invention provides universal GPCR reporter vectors. The constructs comprise a multiple response element (MRE), a cAMP response element, and a serum response element (SRE). Some of the vectors contain a SRE with a sequence of CCXXXXXXGG, wherein X can be A or T. In some of these vectors, the SRE is obtained from human c-fos gene. Some of the vectors contain a SRE that has a sequence of CCATATTAGG.

The universal GPCR reporter vectors can further comprise a reporter gene operably linked to the MRE, the CRE, and the SRE response elements. For example, the reporter gene can be a luciferase gene.

In another aspect, the invention provides host cells that harbor a universal GPCR reporter vector. The vector comprises a multiple response element (MRE), a cAMP response element, and a serum response element (SRE). In some embodiments, the host cell is human embryo kidney 293 (HEK-293) cell stably transfected with the GPCR reporter vector. Some of the host cells can further comprise an exogenous G protein coupled receptor. The G protein coupled receptor in the host cells can be encoded by a polynucleotide introduced into the host cell. The reporter vector in the host cells can also comprise a reporter gene operably linked to the MRE, the CRE, and the SRE response elements.

In another aspect, the invention provides methods for identifying modulators of G protein coupled receptors. The methods entail contacting test agents with a host cell harboring a GPCR and a universal GPCR reporter vector of the invention, and identifying a change of expression level of a reporter gene from the vector. This allows identification of a modulator of the GPCR. Typically, the reporter gene is operably linked to the MRE, the CRE, and the SRE elements in the vector.

In some of these methods, the GPCR is heterologous to the host cell. The heterologous GPCR can be expressed from a second vector that has been introduced into the cell. The GPCR suitable for the methods can be a Gi-coupled receptor, a Gs-coupled receptor, or a Gs-coupled receptor. The modulators to be identified can be an agonist or an antagonist of the GPCR. In some embodiments, the host cell is HEK-293 cell. In some methods, the reporter gene used in the universal GPCR reporter vector is a luciferase gene.

A further understanding of the nature and advantages of the present invention may be realized by reference to the remaining portions of the specification and claims.

DETAILED DESCRIPTION

The practice of the present invention employs, unless otherwise indicated, conventional techniques of molecular biology (including recombinant techniques), microbiology, cell biology, biochemistry and immunology, which are within the skill of the art. Such techniques are explained fully in the literature. For example, exemplary methods are described in the following publications, Sambrook et al., *Molecular Cloning: A Laboratory Manual*, 3d ed. (2001); Ausubel et al., *Current Protocols In Molecular Biology*, (1987)); *Methods In Enzymology* (Academic Press, Inc.); *PCR: A Practical Approach* (M. MacPherson et al., IRL Press at Oxford University Press (1991)); *PCR 2: A Practical Approach* (M. J. MacPherson, B. D. Haines and G. R. Taylor eds. (1995)); *Antibodies, A Laboratory Manual* (Harlow and Lane eds. (1988)); and *Animal Cell Culture* (R. I. Freshney ed. (1987)).

The following sections provide further guidance for making and using the compositions of the invention, and for carrying out the methods of the invention.

I. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). In addition, certain terms may have the following defined meanings. These definitions are provided to assist the reader in the practice of the invention.

As used in the specification and claims, the singular form "an" and "the"include plural references unless the context clearly dictates otherwise. For example, the term "a cell" includes a plurality of cells, including mixtures thereof.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

The term "biological sample" includes any biological material obtained from an individual, a cell line, a tissue culture, or other source. For example, biological samples include tissues, cells, body fluids such as whole blood, serum, plasma, urine, saliva, tears, pulmonary secretions, gastrointestinal secretions, fecal material, lymph fluid, synovial fluid, and cerebrospinal fluid.

As used herein, "contacting" has its normal meaning and refers to combining two or more molecules (e.g., a test agent and a polypeptide) or combining molecules and cells (e.g., a test agent and a cell). Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

The term "expression construct" or "expression vector" means a polynucleotide comprising a promoter element operatively linked to a gene. The expression construct can be formatted in a variety of ways such as in a gene delivery vehicle or inserted into a chromosome of a cell. The term is intended to refer to promoter-gene fusions produced by any method including, but not limited to recombinant DNA techniques, homologous recombination, targeted insertion of a gene or promoter element or random insertion of a gene or promoter element.

The term "homologous" when referring to proteins and/or protein sequences indicates that they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology.

A "host cell," as used herein, refers to a cell into which a heterologous polynucleotide can be or has been introduced. Typically, a host cell of eukaryotic origin is employed. The heterologous polynucleotide can be introduced into the cell by any means, e.g., transfection, electroporation, calcium phosphate precipitation, microinjection, transformation, viral infection, and/or the like.

The term "sequence identity" in the context of two nucleic acid sequences or amino acid sequences refers to the residues in the two sequences which are the same when aligned for maximum correspondence over a specified comparison window. A "comparison window" refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) Adv. Appl. Math. 2:482; by the alignment algorithm of Needleman and Wunsch (1970) J. Mol. Biol. 48:443; by the search for similarity method of Pearson and Lipman (1988) Proc. Nat. Acad. Sci U.S.A. 85:2444; by computerized implementations of these algorithms (including, but not limited to CLUSTAL in the PC/Gene program by Intelligentics, Mountain View, Calif.; and GAP, BESTFIT, BLAST, FASTA, or TFASTA in the Wisconsin Genetics Software Package, Genetics Computer Group (GCG), 575 Science Dr., Madison, Wis., U.S.A.). The CLUSTAL program is well described by Higgins and Sharp (1988) Gene 73:237–244; Higgins and Sharp (1989) CABIOS 5:151–153; Corpet et al. (1 988) Nucleic Acids Res. 16:10881–10890; Huang et al (1992) Computer Applications in the Biosciences 8:155–165; and Pearson et al. (1994) Methods in Molecular Biology 24:307–331. Alignment is also often performed by inspection and manual alignment. In one class of embodiments, the polypeptides herein are at least 70%, generally at least 75%, optionally at least 80%, 85%, 90%, 95% or 99% or more identical to a reference polypeptide, e.g., TMPRSS6, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 95%, 99% or more identical to a reference nucleic acid, e.g., as measured by BLASTN (or CLUSTAL, or any other available alignment software) using default parameters.

A "substantially identical" nucleic acid or amino acid sequence refers to a nucleic acid or amino acid sequence which comprises a sequence that has at least 90% sequence identity to a reference sequence using the programs described above (preferably BLAST) using standard parameters. The sequence identity is preferably at least 95%, more preferably at least 98%, and most preferably at least 99%. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff& Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "modulate" with respect to a reference protein or its fragment refers to a change in one or more biological activity of the protein. For example, modulation may cause an increase or a decrease in expression level of the reference protein, enzymatic modification of the protein, binding characteristics (e.g., binding to a substrate), enzymatic activities of the protein, or any other biological, functional, or immunological properties of the reference protein.

Modulation of a reference protein can be up-regulation (i.e., activation or stimulation) or down-regulation (i.e. inhibition or suppression). The mode of action of a modulator on a reference protein can be direct, e.g., through binding to the protein or to genes encoding the protein, or indirect, e.g., through binding to and/or modifying (e.g., enzymatically) another molecule which otherwise modulates the reference protein.

The term "operably linked" refers to a functional relationship between two or more polynucleotide (e.g., DNA) segments. Typically, it refers to the functional relationship of a transcriptional regulatory sequence to a transcribed sequence. For example, a transcription regulatory sequence is operably linked to a coding sequence if it modulates the transcription of the coding sequence in an appropriate host cell or other expression system. Generally, transcriptional regulatory sequences that are operably linked to a transcribed sequence are physically contiguous to the transcribed sequence, i.e., they are cis-acting. However, some transcription regulatory sequences, such as enhancers or response elements, need not be physically contiguous or located in close proximity to the coding sequences whose transcription they enhance.

The terms "polynucleotide" and "nucleic acid" are used interchangeably to refer to polymeric forms of nucleotides of any length. The polynucleotides may contain deoxyribonucleotides, ribonucleotides, and/or their analogs. Polynucleotides may have any three-dimensional structure, and may perform any function, known or unknown. The term "polynucleotide" includes, for example, single-double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules.

As used herein, a "reporter gene" is a polynucleotide encoding a protein whose expression by a cell can be detected and quantified. Thus, a measurement of the level of expression of the reporter is indicative of the level of activation of the promoter element that directs expression of the reporter gene. Such detection includes, for example, selection for the presence of reporter gene expression by placing cells that contain the reporter gene under selective conditions.

A "subject" is a vertebrate, preferably a mammal, more preferably a human. Mammals include, but are not limited to, murines, simians, humans, farm animals, sport animals, and pets.

A "variant" of a reference molecule refers to a molecule substantially similar in structure and biological activity to either the entire reference molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

II. Universal G-Protein Coupled Receptor Constructs

This invention provides universal GPCR reporter constructs and host cells that contain such reporter constructs. As exemplified in the Examples below, the universal GPCR reporter constructs of the invention can be used to detect the activities of all GPCRs examined in a single functional assay. The reporter constructs contain at least one multiple response element (MRE), a cAMP response element (CRE), and a serum response element (SRE). In addition, the constructs contain a reporter gene that is operably linked to the response elements so that expression of the reporter gene is regulated by the response elements. The reporter gene encodes a product that is readily detectable when expressed in a cell. When a GPCR is also present in the host cell, the presence of a GPCR ligand or modulator will result in an alteration in the level of the reporter gene product.

The response elements employed in the construct, SRE, MRE, and CRE, are all well characterized in the art. Serum response elements are promoter elements required for the regulation of many cellular immediate-early genes by growth. SREs from various genes (e.g., c-fos gene) have been described in the art, e.g., in Treisman, R., *The serum response element*, TIBS, 17:423–426, 1992. Any of these SRE elements can be used to construct the universal GPCR reporter construct of the present invention. In some embodiments, the SRE used has an inner core consensus sequence of CCXXXXXXGG (SEQ ID NO: 1) wherein X can be either A or T (U.S. Pat. No. 6,423,693). In some other embodiments, the SRE used to make the reporter constructs has a core sequence of CTXXXXXXGG (SEQ ID NO: 2) wherein X can be either A or T (Hines et al., Mol. Cell. Biol. 19:1841–52, 1999).

MREs, or multiple response elements, are enhancer elements that confer responsiveness to multiple cytokines and second messengers. One example of MREs is a 32-bp sequence from the promoter of the IL-6 gene (−173 to −142 region; Ray et al., Mol. Cell. Biol. 9: 5537–47, 1989). It confers upon the heterologous herpesvirus thymidine kinase (TK) promoter responsiveness to reagents such as serum, forskolin, and phorbol ester. In some embodiments, this IL-6 derived MRE is employed in the universal GPCR reporter constructs of the present invention. In some other embodiments, fragments a MRE or variants with substantial identical sequences to a MRE are used to construct the universal GPCR reporter vectors. For example, other than the IL-6 MRE sequence noted above, the MRE used in the constructs can be a 23 bp fragment of the IL-6 promoter (-173 to -151 region; Ray et al., Mol. Cell. Biol. 9: 5537–47, 1989). In some constructs, several copies of a MRE can be included, as exemplified in the Examples below.

CRE, or cAMP response element, is a transcription regulatory sequence that interacts with transcription factors which mediate signal transduction involving cAMP. A consensus sequence has been described for CRE enhancers, comprising 5'-TGACGTCA-3' (Roesler et al., J. Biol. Chem. 263: 9063–66, 1988). In addition to this sequence, the universal GPCR reporter construct of the present invention can also employ CREs from many genes that deviate from this consensus sequence. Such sequences include, but are not limited to, TTACGTCA (Short et al., J. Biol. Chem. 261, 9721, 1986), TGACGTCT (Tsukada et al., J. Biol. Chem. 262, 8743, 1987), TGACGTAG (VanBeveren et al., Cell 32, 1241, 1983), and CTGCGTCA (Comb et al., Nature 323, 353, 1986).

Typically, in the universal GPCR reporter constructs, the response elements are operatively linked to a reporter gene that functions to identify the presence or absence of ligand-activated GPCR. The reporter genes include a polynucleotide that encodes a selectable or detectable polypeptide. Examples of genes useful as reporter genes include, e.g., genes that encode a metabolic enzyme, an antibiotic resistance factor, a luminescent protein, or a fluorescent protein. Such reporter genes are well known in the art and particular examples are described in Wood (1995) *Curr. Opin. Biotechnol.* 6(1):50–58. In some constructs of the invention, the reporter gene encodes luciferase. In some other embodiments, the reporter gene encodes a metabolic enzyme such as β-galactosidase. In some constructs, the reporter gene is a gene that complements an auxotrophic mutation in a host cell and allows growth of cells that express the gene on selective media.

Selection of appropriate reporter genes will enable the use of this universal GPCR reporter assay system in a variety of efficient, high-throughput procedures to rapidly screen large number of compounds in order to identify agonists or antagonists that specifically bind to a given GPCR. The ease of detection of reporter genes such as β-gailactosidase. luciferase, and green fluorescent protein further provides for the development of automated procedures to screen for modulators of a given GPCR.

Methods for detecting and quantitating reporter expression are commonly based on measuring the activity of the protein encoded by the reporter. A wide variety of appropriate detectable markers are known in the art, including fluorescent, radioactive, enzymatic or other ligands, such as avidin/biotin, which are capable of giving a detectable signal. In some embodiments, one can employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically.

When the reporter is an enzyme, a substrate for the enzyme which is metabolized to produce a measurable product can be used. For example, the β-galactosidase substrate X-gal, which is cleaved by this enzyme to produce a blue reaction product, is frequently used to assay P-galactosidase reporter expression. (Miller J. ed. (1992) *A Short Course in Bacterial Genetics: A Laboratory Manual and Handbook for Escherichia Coli and Related Bacteria*, Cold Spring Harbor Laboratory, Cold Spring Harbor, N.Y. Alternatively, the β-galactosidase substrate o-nitrophyl-B-D-galactopyranoside (ONPG), which is metabolized by β-galactosidase to produce a compound with a yellow color. The quantity of enzyme is determined by measuring optical density of the colored compound spectrophotometrically or with an ELISA reader. The absorbance is read at 420 nm (Miller J. H. ed. (1972) *Experiments in Molecular Genetics*, Cold Spring Harbor Laboratory, Cold Spring Harbor, N.Y.). Other commonly used reporter genes are the antibiotic resistance factor chloramphenicol acetyl transferase (CAT), the firefly luciferase gene (as shown in the Examples below), and the jellyfish green fluorescent protein (Valdivia and Falkow (1997) *Trends Microbiol.* 5(9):360–363; Naylor (1999) *Biochem. Pharmacol.* 58(5):749–757; Himes and Shannon (2000) *Methods Mol. Biol.* 130:165–174). In addition, a variety of alternative proteins can also be used as reporters based on their ability to be detected and quantitated. Assays to measure the expression levels of such genes are well developed and are commonly practiced by those of ordinary skill (Rosenthal (1987) *Methods Enzymology* 152: 704–720; Davey et al. (1995) *Methods Mol. Biol.* 49:143–148; and Bronstein et al. (1994) *Anal. Biochem.* 219(2):169–181).

Polynucleotides that encode useful reporter genes are available from a variety of commercial suppliers of molecular biology reagents such as LifeTechnologies Inc. (Gaithersburg, Md.), Clontech Inc. (Palo Alto, Calif.), Promega Inc. (Madison, Wis.), Invitrogen Inc. (Carlsbad, Calif.), and Strategene Inc. (San Diego, Calif.). In addition, plasmid vectors comprising reporter gene sequences are available from the American Type Culture Collection and genetic repositories such as the *E. coli* strain collection at Yale University.

The universal GPCR reporter constructs of the invention can comprise additional sequences. These include coding sequences within the same transcription unit, controlling elements such as ribosome binding sites, and polyadenylation sites, additional transcription units under control of the same or a different promoter, sequences that permit cloning, expression, and transformation of a host cell. In some embodiments, the universal GPCR reporter constructs include a polynucleotide that encodes a signal peptide that directs a detectable polypeptide encoded by the reporter gene to a surface of the host cell. The detectable polypeptide can then be detected by, e.g., a cell sorter. For example, if the reporter gene encodes a fluorescent protein, which is displayed on the surface of the cell upon expression, one can utilize a fluorescence activated cell sorter to separate cells that express the reporter gene from those that do not.

The universal GPCR reporter constructs can also include a polynucleotide that encodes a molecular tag that can facilitate separation of a host cell that expresses the reporter gene from a host cell that does not express the reporter gene. For example, an epitope for an antibody can function as a molecular tag; cells that express the reporter gene can then be immobilized by contacting the cells with a solid support to which is attached antibodies that specifically recognize the epitope. Other suitable molecular tags are well known to those of skill in the art, for example, a FLAG™ peptide.

The polynucleotides and sequences (e.g., the response elements) embodied in this invention can be obtained using chemical synthesis, recombinant cloning methods, PCR, or any combination thereof. The PCR technology is the subject matter of U.S. Pat. Nos. 4,683,195; 4,800,159; 4,754,065; and 4,683,202 and described in PCR: THE POLYMERASE CHAIN REACTION (Mullis et al. eds, Birkhauser Press, Boston (1994)) or MacPherson et al. (1991) and (1995), supra, and references cited therein. Alternatively, one of skill in the art. can use the sequences provided herein and a commercial DNA synthesizer to replicate the DNA.

III. Host Cells and Assay Systems for Detecting Activities of GPCRs

The invention provides host cells for harboring the universal GPCR reporter constructs. Also provided are assay systems and methods for detecting activities of various GPCRs, e.g., for identifying modulators of GPCRs especially orphan receptors. The methods comprise culturing a host cell that harbors a universal GPCR reporter construct described above. The host cell also expresses a GPCR of which activities are to be detected. The GPCR can be endogenous to the host cells. Alternatively, the GPCR can be heterologous to the host cell. The exogenous GPCR can be expressed from a polynucleotide that has been introduced into the host cell, e.g., an expression vector stably expressing a GPCR (HEK293 cells as demonstrated in the Examples below). The host cell is cultured under conditions in which the GPCR is expressed. Test compounds or a biological sample containing potential modulators (agonists or antagonists) of the receptor are then put into contact with the cell. The level of expression of the reporter gene from the universal GPCR reporter construct is then monitored relative to its expression level in the absence of the test compounds or the biological sample. An alteration (increase or decrease) of the expression level indicates that a modulator (agonist or antagonist) of the GPCR is present.

1. Host cells

Various cells types can be employed to harbor the universal reporter constructs. Preferably, host cells of eukaryotic origins are used. Suitable eukaryotic host cells harboring the universal reporter construct include, for example, mammalian, insect, or plant cells or microorganisms, such as, for example, yeast cells or fungal cells. Suitable mammalian host cells include, e.g., HCT116, HEK 293, MCF-7, Jurkat cells, NIH3T3 cells, and HepG2 cell lines.

2. Functional Assays to Identify Modulators of GPCR's

The various GPCRs are important to the normal and sometimes aberrant functions of many cell types (see generally Strosberg, Eur. J. Biochem. 196: 1–10, 1991; and Bohm et al., Biochem J. 322: 1–18, 1997). Because of the vital role of G protein-coupled receptors in the communication between cells and their environment, such receptors are attractive targets for therapeutic intervention by using drugs that activate or antagonize the activation of such receptors. The GPCR reporter constructs and host cells described herein are useful to identify novel ligands or modulators (agonists or antagonists) of various GPCRs. For example, they can be used to screen for agonists or antagonists of GPCRs of which no ligands have been identified (orphan receptors). For receptors having a known ligand, the identification of novel agonists or antagonists may be sought specifically for mimicking, enhancing or inhibiting the action of the ligand.

Typically, a host cell harboring a universal GPCR reporter vector of this invention is cultured under conditions to allow expression of an endogenous GPCR or an exogenous GPCR encoded by a polynucleotide that has been introduced into the cell. Test agents or a biological sample containing a potential modulator of the GPCR are put into contact with the cell. Expression of the reporter gene is measured thereafter. This can be accomplished by measuring the amount of protein directly such as by measuring fluorescence of a fluorescent protein or by measuring the reporter protein by an immunoassay such as an ELISA assay. Alternatively, if the reporter gene is an enzyme, the amount of reporter produced can be measured using an assay that quantifies a product produced by enzymatic modification of a substrate compound, such as metabolism of X-gal or ONPG by the β-galactosidase enzyme.

Modulation of the reporter gene expression due to ligand binding to a GPCR can be determined by comparing expression level of the reporter gene in the presence of the test compound to its expression level in a control cell. The control can be the host cell harboring the reporter construct and the GPCR that has been cultured in the absence of the test compound. Additional control includes a host cell harboring the reporter construct but not the GPCR that has been cultured in the presence of the test agent. If a test agent alters expression level of the reporter gene relative to expression level of the reporter gene in the controls, the test agent is identified as a modulator of the GPCR. If the GPCR has a known ligand, the alteration of reporter gene expression by a test agent can also be measured quantitatively. This include first preparing a standard curve correlating expression level of the reporter gene in the host cell with the concentration of the known GPCR ligand in the culture medium. This can be accomplished by culturing the host cell comprising the reporter construct together with the GPCR in a series of samples in which various amounts of the known ligand are added to the culture media. Expression of the reporter gene is measured in each of these samples.

Typically, a potential ligand or modulator of the GPCR is identified if there is a significant departure of expression level of the reporter gene from its basal level of expression (e.g., expression levels in the control cells). The departure is significant if the expression level is at least a 50%, preferably at least 75%, and more preferably at least 90% different from the basal level. In some embodiments, expression level of the reporter gene can be altered by several folds within certain period (e.g., 1, 5, or 24 hours) upon binding of a ligand to the GPCR.

Test agents that can be employed to identify ligands or modulators of GPCRs include molecules of various chemical natures. They can be synthetic compounds or natural molecules. For example, they can be small chemical compounds, polypeptides, nucleic acids, beta-turn mimetics, polysaccharides, phospholipids, hormones, prostaglandins, steroids, and their analogs. In some preferred embodiments, the test agents are small molecules (e.g., molecules with a molecular weight of not more than about 1,000). The test agents can also be biological samples obtained from various natural resources. For example, a cell lysate, tissue, or body fluid, can all be used to identify potential ligands of GPCRs with methods of the present invention.

3. High-throughput screening

The assays for identifying compounds capable of modulating GPCRs can be adapted in high-throughput screening format. High-throughput screening refers to methods for simultaneously assaying a large number of test compounds for their ability to bind to a target GPCR. A high throughput assay format allows for a wide variety of test compounds to be screened rapidly and efficiently for their respective effects on GPCRs. This format allows larger numbers of test compounds to be screened simultaneously minimizing differences in assay components and conditions, thereby diminishing variability of results unrelated to test compound activity. High throughput screening methods involve providing a library containing a large number of test compounds. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries are well known to those of skill in the art (see, generally, Gordon et al., J. Med. Chem. 37:1385–1401, 1994). Such combinatorial libraries include libraries of small organic compound libraries (see, e.g., Chen et al., J. Amer. Chem. Soc. 116: 2661, 1994; and U.S. Pat. Nos. 5,569,588; 5,549,974; 5,525,735; 5,519,134; 5,506,337; and 5,288,514). They also include nucleic acid libraries (Jin et al., Bioorg Med Chem Lett. 10:1921–5,2000; and Deutscher et al., Arch Biochem Biophys. 333(1):207–13, 1996); peptide libraries (see, e.g., U.S. Pat. Nos. 5,010,175 and 5,539,083), antibody libraries (see, e.g., Vaughn et al., Nature Biotechnology, 14: 309–314, 1996), and carbohydrate libraries (see, e.g., Liang et al. Science, 274: 1520–1522, 1996), and random biooligomers (PCT Publication WO 92/00091). Combinatorial libraries that can be employed to practice the present invention further include libraries of vinylogous polypeptides (Hagihara et al., J. Amer. Chem. Soc. 114: 6568, 1992), nonpeptidal peptidomimetics with a Beta D Glucose scaffolding (Hirschmann et al., J. Amer. Chem. Soc. 114: 9217–18, 1992), oligocarbamates (Cho, et al., Science 261:1303, 1993), and peptidyl phosphonates (Campbell et al., J. Org. Chem. 59: 658, 1994). Numerous combinatorial libraries are commercially available (see, e.g., ComGenex, Princeton, N.J., Asinex, Moscow, Ru, Tripos, Inc., St. Louis, Mo., ChemStar, Ltd. Moscow, RU, 3D Pharmaceuticals, Exton, Pa., Martek Biosciences, Columbia, Md., etc.). In addition, devices for the preparation of combinatorial libraries are also commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

High throughput screening can be performed by using commercially available automated instruments, software, and known automated observation and detection procedures. Multi-well formats are particularly attractive for high throughput and automated compound screening. Screening methods can be performed, for example, using a standard microtiter plate format, with a test compound in each well of the microtiter plate. This format permits screening assays to be automated using standard microtiter plate procedures and microtiter plate readers to detect binding of test compounds to GPCRs. A microplate reader includes any device that is able to read a signal from a microtiter plate (e.g., 384 well plate) including fluorometry (standard or time-resolved), luminometry or photometry in either endpoint or kinetic assays. Using such techniques, the effect of a specific agent upon a GPCR can be ascertained using an extremely small reaction volume.

For example, the automated high throughput screening systems can be commercially obtained from, e.g., Zymark Corp., Hopkinton, Mass.; Air Technical Industries, Mentor, Ohio; Beckman Instruments, Inc. Fullerton, Calif.; Precision Systems, Inc., Natick, Mass., etc. These systems typically automate entire procedures including all sample and reagent pipetting, liquid dispensing, timed incubations, and final readings of the microplate in detector(s) appropriate for the assay. These configurable systems provide high throuput and rapid start up as well as a high degree of flexibility and customization. The manufacturers of such systems provide detailed protocols for carrying out the various high throughput screening assays. Thus, for example, Zymark Corp. provides technical bulletins describing screening systems for detecting the modulation of gene transcription, ligand binding, and the like.

EXAMPLES

The following examples are offered to illustrate, but not to limit the present invention.

Example 1

Construction of a Universal GPCR Reporter Construct

We first constructed a reporter gene construct containing the multiple-response element and the cAMP-response element, MRE/CRE-pGL3-basic, as described in Fitzgerald et al., Analyt. Biochem. 275: 54–61, 1999. This construct also contains a luciferase reporter gene. The construct was then further modified by insertion of a serum-response element (SRE) from the human c-fos gene. SRE sense and antisense oligonucleotides were synthesized and purified by polyacrylamide gel. The SRE sense sequence is 5'-GCGAGCTCT-TACACAGGATGTCCATATTAGGACATCT-GCGTCAGCAGGTTTCCA CGGCCACGCGCTGC (SEQ ID NO: 3). The antisense sequence is 5-GCACGCGTGGC-CGTGGAAACCTGCTGACGCAGATGTC-CTAATATGGACATCCTG TGTAAGAGCTCGC (SEQ ID NO: 4). These two oligonucleotides were mixed at 1:1 ratio (1 µM each) in 10 mM Tris-HCl, pH 7.5, 10 mM $MgCl_2$, and 0.1 mg/ml BSA and incubated at 70° C. for 30 min, 37° C. for 30 min, and room temperature for 30 min. During the incubation, the two oligonucleotides should form double-stranded DNA. It was digested with restriction enzymes SacI and MluI at 37° C. for 3 h. The digested DNA product was subcloned into SacI and MluI-digested MRE/CRE-pGL3-basic vector to create MRE/CRE/SRE-pGL3-basic reporter gene construct.

Example 2

GPCR Universal Functional Assay

Human GPCR cloning: PCR was carried out to clone cDNAs of human GPCRs using Pfu DNA polymerase (Promega). Human genomic DNA was used as template for the PCR cloning. The PCR products were cloned into pCR2.5-TOPO vector and subsequently subcloned into mammalian expression vector pCDNA3.1 (Invitrogen). The cDNA clones were confirmed by DNA sequencing.

Transfection and stable cell line selection: HEK-293 cells were cultured in DMEM (high glucose) with 10% inactivated fetal bovine serum, 0.1 mM nonessential amino acids, 1 mM sodium pyruvate, and antibiotics (Life Technology). FuGENE6 transfection reagent (Boehringer-Mannheim) was used for all transfection experiments based on the manufacturer's protocol. The ratio of human GPCRs in pCDNA3.1 to reporter gene constructs was 1:5. Forty-eight hours after transfection, several individual cell lines were selected by 800 µg/ml G418 (Life Technology).

Luciferase assay: Cells were plated in 96-well white, clear-bottom plates (Corning) at $4 \times 10^4$ cells/well in 100 µl medium and incubated at 37° C. overnight. Ligands at different concentrations were dissolved in 11 µl medium and added to each well. The cells were incubated at 37° C. for 6 h. One hundred microliters of Bright-Glo (Promega) was added to each well. Then, the luminescence signal was measured immediately using Acquest (LJL Biosystems).

Universal reporter assay system: the GPCR reporter construct described herein was tested for its usefulness for various GPCRs. We first examined the MRE/CRE/luciferase reporter construct as described in Fitzgerald et al. (Analyt. Biochem. 275: 54–61, 1999). This reporter construct contains the MRE and CRE response elements. A total of more than 20 different GPCRs were examined. The results demonstrated that this system could be used to detect activities of some these GPCRs. For example, we tested a number of neuropeptide receptors, such as human melanocortin 4 (MC4), melanocortin 3 (MC3), neuromedin U 2 (NMU2), and neuropeptide Y 5 (NPY5) receptors. However, this reporter system does not detect all GPCRs. For example, we examined small molecule neurotransmitter acetylcholine, serotonin, and dopamine receptors in this reporter gene assay. The results showed that the activities of muscarinic MI and dopamine DI receptors, but not 5HT2C receptor, were detectable.

To find out whether the 5HT2C cell line expressed the MRE/CRE/Luciferase reporter gene construct, we treated the cell line with forskolin to activate adenyl cyclase. Our result showed that forskolin could stimulate the reporter gene system. We next tested whether the cell line also expressed 5HT2C receptor using the fluorometric imaging plate reader (FLIPR) assay. The intracellular calcium concentration was increased upon serotonin stimulation. These results demonstrated that the cell line expressed both the 5HT2C receptor and the reporter gene construct. It is clear from these data that the reporter gene assay described in Fitzgerald et al. does not function universally for all GPCRs.

Employing the universal GPCR reporter construct described herein, we examined its activity in detecting activities of various GPCRs. The results indicated that this reporter construct was able to successfully detect the activity of 5HT2C receptors as well as other GPCRs that either do not or very weakly respond to the MRE/CRE/Luciferase reporter gene (Table 1). Subsequently, we used the modified reporter gene system to test more than 20 different GPCRs, including neuropeptides and small molecule neurotransmitter Gs-, Gi-, and Gq-coupled receptors. Our results demonstrated that the new reporter gene assay could be used to detect activities of all GPCRs (Table 1).

TABLE 1

Universal functional assay for G-protein-coupled receptors

| GPCRs | G-protein | Reporter gene constructs | Activity |
| --- | --- | --- | --- |
| Human MC1 | Gs | MRE/CRE and RE/CRE/SRE | High/high |
| Human MC2 | Gs | MRE/CRE and MRE/CRE/SRE | High/high |
| Human MC3 | Gs | MRE/CRE and MRE/CRE/SRE | High/high |
| Human MC4 | Gs | MRE/CRE and MRE/CRE/SRE | High/high |
| Mouse MC1 | Gs | MRE/CRE and MRE/CRE/SRE | High/high |
| Mouse MC2 | Gs | MRE/CRE and MRE/CRE/SRE | High/high |
| Mouse MC3 | Gs | MRE/CRE and MRE/CRE/SRE | High/high |
| Mouse MC4 | Gs | MRE/CRE and MRE/CRE/SRE | High/high |
| Mouse MC5 | Gs | MRE/CRE and MRE/CRE/SRE | High/high |
| Human NMU1 | Gq | MRE/CRE and MRE/CRE/SRE | Low/high |
| Human NMU2 | Gq | MRE/CRE and MRE/CRE/SRE | Low/high |
| Human 5HT2C | Gq | MRE/CRE and MRE/CRE/SRE | No/high |
| Human orexin2 | Gq | MRE/CRE and MRE/CRE/SRE | High/high |
| Human MCH1 | Gi | MRE/CRE and MRE/CRE/SRE | High/high |
| Human M1 | Gq | MRE/CRE and MRE/CRE/SRE | Low/high |
| Human D1 | Gs | MRE/CRE and MRE/CRE/SRE | High/high |
| Human D5 | Gs | MRE/CRE and MRE/CRE/SRE | High/high |
| Human A1 | Gi | MRE/CRE and MRE/CRE/SRE | High/high |
| Human A2α | Gs | MRE/CRE and MRE/CRE/SRE | High/high |
| Human A3 | Gi | MRE/CRE and MRE/CRE/SRE | High/high |
| Human PTH | Gs | MRE/CRE | High |
| Human C5α | Gq | MRE/CRE | High |
| Human NPY5 | Gi | MRE/CRE and MRE/CRE/SRE | High/high |
| Human Glu | Gs | MRE/CRE and MRE/CRE/SRE | High/high |

Twenty-four different GPCRs were tested using the universal functional assay.
All tests were performed in stably transfected HEK-293 cells (Materials and methods).
MC, melanocortin;
NMU, neuromedin U;
MCH, melanin concentrating hormone;
M, muscarinic;
D, dopamine;
A, adenosine;
NPY, neuropeptide Y;
Glu, glucagon;
PTH, parathyroid hormone.

It is understood that the examples and embodiments described herein are for illustrative purposes only and that various modifications or changes in light thereof will be suggested to persons skilled in the art and are to be included within the spirit and purview of this application and scope of the appended claims.

All publications, GenBank sequences, ATCC deposits, patents and patent applications cited herein are hereby expressly incorporated by reference in their entirety and for all purposes as if each is individually so denoted.

We claim:

1. A polynucleotide vector comprising a multiple response element (MRE), a cAMP response element (CRE) and a serum response element (SRE).

2. The vector of claim 1, wherein the SRE comprise a sequence of CCXXXXXXGG (SEQ ID NO: 1) wherein X is A or T.

3. The vector of claim 1, wherein the SRE is from human c-fos gene.

4. The vector of claim 1, wherein the SRE comprises a sequence of CCATATTAGG (SEQ ID NO: 5).

5. The vector of claim 1, further comprising a reporter gene operably linked to the MRE, the CRE, and the SRE.

6. The vector of claim 5, wherein the reporter gene is a luciferase gene.

7. A host cell comprising a polynucleotide vector that comprises a multiple response element (MRE), a cAMP response element (GRE), and a serum response element (SRE).

8. The host cell of claim 7 which is human embryo kidney 293 (HEK-293) cell stably transfected with the vector.

9. The host cell of claim 7, further comprising an exogenous G protein coupled receptor.

10. The host cell of claim 9, wherein the G protein coupled receptor is encoded by a polynucleotide introduced into the host cell.

11. The host cell of claim 7, further comprising a reporter gene operably linked to the MRE, the GRE, and the SRE.

12. A method for identifying a modulator of a G protein coupled receptor (GPCR), comprising (i) contacting a test agent with a host cell comprising the GPCR and a universal GPCR reporter vector, and (ii) identifying a change of expression level of a reporter gene from the vector relative to expression level of the reporter gene in the absence of the test agent; thereby identifying a modulator of the GPCR; wherein the GPCR reporter vector comprises a MRE, a GRE, and a SRE that are operably linked to the reporter gene.

13. The method of claim 12, wherein the GPCR is heterologous to the host cell.

14. The method of claim 13, wherein the GPCR is expressed from a second vector that has been introduced into the cell.

15. The method of claim 12, wherein the GPCR is a Gi-coupled receptor, a Gs-coupled receptor, or a Gs-coupled receptor.

16. The method of claim 12, wherein the modulator is an agonist of the GPCR.

17. The method of claim 12, wherein the modulator is an antagonist of the GPCR.

18. The method of claim 12, wherein the host cell is HEK-293 cell.

19. The method of claim 12, wherein the reporter gene is a luciferase gene.

* * * * *

SEQUENCE LISTING

<160> NUMBER OF SEQ ID NOS: 5

<210> SEQ ID NO 1
<211> LENGTH: 10
<212> TYPE: DNA
<213> ORGANISM: Homo sapiens
<220> FEATURE:
<221> NAME/KEY: misc_feature
<223> OTHER INFORMATION: "W" is "A" or "T"

<400> SEQUENCE: 1 ccwwwwwwgg                                                          10

<210> SEQ ID NO 2
<211> LENGTH: 10
<212> TYPE: DNA
<213> ORGANISM: Homo sapiens
<220> FEATURE:
<221> NAME/KEY: misc_feature
<223> OTHER INFORMATION: "W" is "A" or "T"

<400> SEQUENCE: 2 ctwwwwwwgg                                                          10

-continued

```
<210> SEQ ID NO 3
<211> LENGTH: 67
<212> TYPE: DNA
<213> ORGANISM: Homo sapiens

<400> SEQUENCE: 3
gcgagctctt acacaggatg tccatattag gacatctgcg tcagcaggtt tccacggcca      60
cgcgtgc                                                                67

<210> SEQ ID NO 4
<211> LENGTH: 67
<212> TYPE: DNA
<213> ORGANISM: Homo sapiens

<400> SEQUENCE: 4
gcacgcgtgg ccgtggaaac ctgctgacgc agatgtccta atatggacat cctgtgtaag      60
agctcgc                                                                67

<210> SEQ ID NO 5
<211> LENGTH: 10
<212> TYPE: DNA
<213> ORGANISM: Homo sapiens

<400> SEQUENCE: 5
ccatattagg                                                             10
```